United States Patent [19]

Kaster et al.

[11] Patent Number: 4,512,471
[45] Date of Patent: Apr. 23, 1985

[54] STORAGE UNIT

[75] Inventors: Robert L. Kaster, Plymouth; Perry M. Domaas, Brooklyn Center, both of Minn.

[73] Assignee: Angicor Limited, Minneapolis, Minn.

[21] Appl. No.: 597,796

[22] Filed: Apr. 6, 1984

[51] Int. Cl.³ .............................................. B65D 85/02
[52] U.S. Cl. ..................... 206/438; 206/526; 206/216; 3/1.5; 220/4 E
[58] Field of Search ............... 206/526, 205, 438, 523, 206/216, 5.1; 215/6; 220/4 E, 4 B; 3/1.5

[56] References Cited

U.S. PATENT DOCUMENTS

| | | | |
|---|---|---|---|
| 2,833,436 | 5/1958 | Ruderian | 215/6 |
| 4,049,277 | 9/1977 | Carlsson, Jr. et al. | 215/6 |
| 4,101,031 | 7/1978 | Cromie | 206/523 |
| 4,171,743 | 10/1979 | Mascia et al. | 220/4 E |
| 4,182,446 | 1/1980 | Penny | 206/205 |
| 4,211,325 | 7/1980 | Wright | 206/438 |

Primary Examiner—William T. Dixson, Jr.
Attorney, Agent, or Firm—Henderson & Sturm

[57] ABSTRACT

A storage unit for use in storing a prosthetic heart valve in conjunction with a plurality of heart valve orifice measurement gauges that includes separate container units (11 and 12), which container units can be selectively connected and disconnected by a connecting unit (13). Opening units (14) are provided for each container unit (11 and 12) to allow access to secondary container units (16) contained therein. The secondary container units contain separately the prosthetic heart valve and heart valve orifice measurement gauges under sterile conditions. Object indicia (18) are provided on the container units (11 and 12) to indicate the contents and size of the heart valve stored within the storage unit. Substantially opaque package unit envelops the first and second container units (11 and 12), though a window unit (21) is provided to allow visual observation of the object indicia (18).

10 Claims, 11 Drawing Figures

Sterile

Non Sterile

STORAGE UNIT

TECHNICAL FIELD

This invention relates generally to containers, and more particularly to storage units as used for the containment of prosthetic heart valves and heart valve orifice measuring gauges.

BACKGROUND ART

The human heart has four one-way valves that aid in regulating the flow of blood therethrough. When one of these natural heart valves becomes damaged, it sometimes becomes necessary to replace the damaged natural heart valve with a prosthetic one.

Natural heart valves occur in a variety of sizes; therefore, prosthetic heart valves are provided in a similar variety of sizes. In order to properly support heart valve implantation surgery, a hospital must maintain a full inventory of these differently sized heart valves. Such inventorized heart valves must be maintained, protected against physical damage, sterile, and in such a manner as to allow quick access to a particular sized heart valve.

Typically, such a medical facility will also own one or more sets of heart valve orifice measuring gauges as well. Such gauges are used to correctly gauge the size of the natural heart valve orifice to insure the selection of a properly sized prosthetic heart valve.

The applicant has previously invented a new heart valve orifice measuring gauge (see U.S. patent application Ser. No. 597,795). Amongst other unique features, this new gauge is very small in size and can be disposed of after use, thereby avoiding the need for resterilization and restorage.

Ideally, a hospital will maintain an inventory of such disposable gauge sets in a quantity equal to the number of prosthetic heart valves that are then in storage. In this way, the medical facility can be assured that it will have a supply of gauges that will support the supply of heart valves. Unfortunately, current containers as used with heart valves are completely independent of current containers as used with heart valve orifice measuring gauges. This would force a hospital to assume additional inventory responsibilities if it wishes to take advantage of the convenience of using disposable gauge sets; i.e., a proper inventory of heart valves must be maintained as before, and an additional proper inventory of gauge sets must be managed as well.

There therefore exists a need for a storage unit that would allow a disposable gauge set to be shipped and stored in inventory with prosthetic heart valves. This storage unit must allow the gauges to be accessed for use without violating the sterility of the heart valve containment vessel. This storage unit should allow that particular heart valve to be returned to storage if it is found to be the wrong size as determined by a gauge reading, and should further allow the unused gauge set associated with the correct sized heart valve to be joined with the first heart valve container. This would maximize convenience and avoid the need for a dual inventory record.

DISCLOSURE OF THE INVENTION

These needs and others are substantially met through provision of the storage unit as disclosed herein. This storage unit includes generally first and second container units for containing a prosthetic heart valve and a gauge set, respectively, object indicia, and a package unit.

The first and second container units each include an opening unit for allowing access to the interior thereof. The first and second container units each also include a sterile secondary container unit disposed therein for containing the prosthetic heart valve or gauge set, as appropriate.

The first and second container units may be selectively connected and disconnected from one another through a connecting unit. This connecting unit includes a plurality of tabs disposed on the first container unit and a plurality of notches formed on the second container unit. When these tabs and notches are interconnected with one another, the first and second container units can be locked together. Conversely, when these tabs and notches are disengaged, the first and second container units can be separated.

Importantly, the opening unit for the first container unit allows the contents of the first container unit to be accessed without disturbing the sterility of the contents of the second container unit, and vice-versa.

The object indicia comprises a label or other indicia affixed to the exterior of the container units. By consulting the object indicia, the observer will be informed as to the contents of the storage unit, including the size of the prosthetic heart valve contained therein.

The package unit comprises a substantially opaque styrofoam package that envelops and protects the first and second container units. In addition, the package unit includes one or more windows disposed therethrough such that the object indicia on the container units can be viewed.

Finally, a sleeve unit may be provided for at least partially enveloping the opaque package unit, without occluding the window or the object indicia.

Through use of this storage unit, a prosthetic heart valve and a gauge set may be jointly maintained in inventory by a medical facility.

During a prosthetic heart valve implantation operation, one such storage unit may be removed from inventory, and the gauge set associated with it accessed. The gauges may then be utilized to determine the size of the heart valve orifice. If the first prosthetic heart valve removed from inventory coincides with this size, then it may be used. If it does not, then the surgeon or assistant may return to inventory and obtain a correct sized heart valve, as determined by viewing the object indicia.

The gauge set associated with the second heart valve can be removed from that storage unit and then connected to the container unit for the first heart valve. The combined first and second container units can then be restored to inventory within the package unit. The object indicia for that particular heart valve size will again be visible through the window such that the heart valve remains available as needed.

The storage unit is comprised of a substantially durable material so that it may be transported and stored without excessive caution in safeguarding either the storage unit or the contents within. The storage unit is capable of withstanding substantial impact or pressure that may be incurred during transportation or storage of said storage unit.

Through use of this invention, then, the full benefits of the inventors new heart valve orifice measurement gauges can be realized.

BRIEF DESCRIPTION OF THE DRAWINGS

These and other attributes of the invention will become more clear upon a thorough review and study of the following description of the best mode for carrying out the invention, particularly when reviewed in conjunction with the drawings, wherein.

BEST MODE FOR CARRYING OUT THE INVENTION

Figure 9:
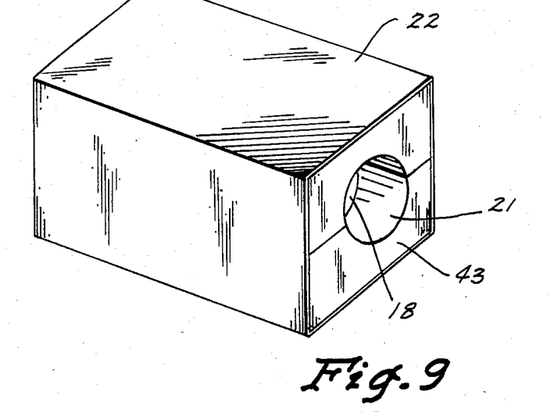
FIG. 9 comprises a perspective view of the package unit.

Referring now to the drawings, the apparatus can be seen as depicted generally by the numeral 10. The apparatus (10) includes more particularly a first and second container unit (11 and 12) (FIG. 1), a connecting unit (13) (FIG. 2), an opening unit (14) (FIG. 3) for each container unit (11 and 13), a secondary container unit (16) (FIG. 5) disposed within each container unit (11 and 12), a secondary container opening unit (17) (FIG. 6) for each secondary container (16), object indicia (18) (FIG. 11), and a package unit (19) (FIG. 10) that includes a window unit (21) (FIG. 10) and a sleeve unit (22) (FIG. 9). Each of these units will now be described in more detail in seriatum fashion.

Figure 2:
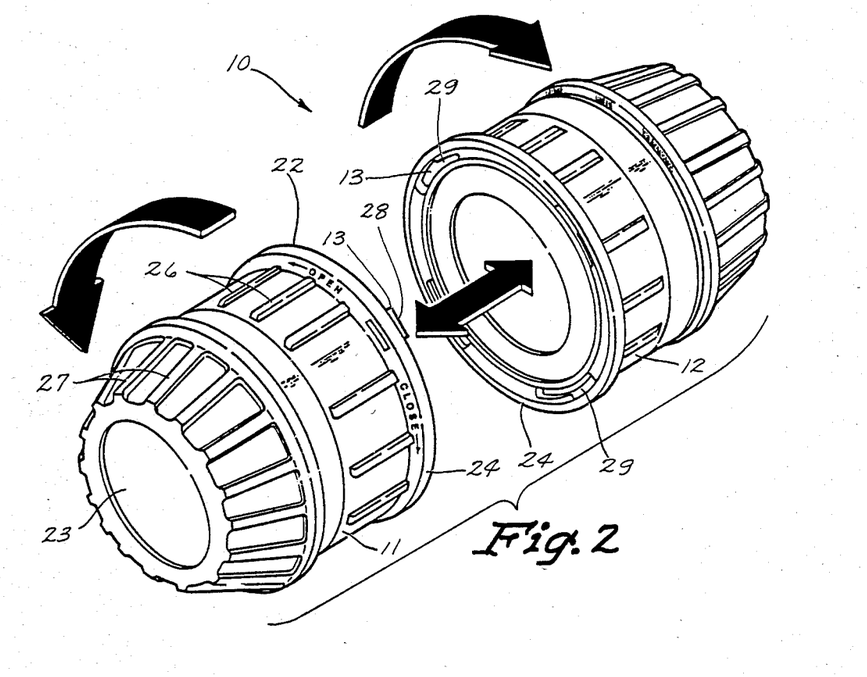
FIG. 2 comprises a perspective view of the first and second container units as separated from one another.

Referring to FIG. 2, the first and second container units (11 and 12) are generally comprised of two substantially identical containers. Therefore, only one (11) will be described in detail, with differences between the two being noted where appropriate.

The container unit (11) may be comprised of plastic or any other suitable material, and has a base unit (22) and a cap unit (23). The base unit (22) has a rim (24) formed about the end periphery thereof for accommodating the connecting unit (13) as described in more detail below.

The cap unit (23) may be formed in the shape of a truncated cone and also includes a plurality of ridges (27) formed thereon to facilitate grasping of the cap unit (23). As will be disclosed in more detail below, the cap unit (23) may be selectively removed from the base unit (22).

Figure 1:
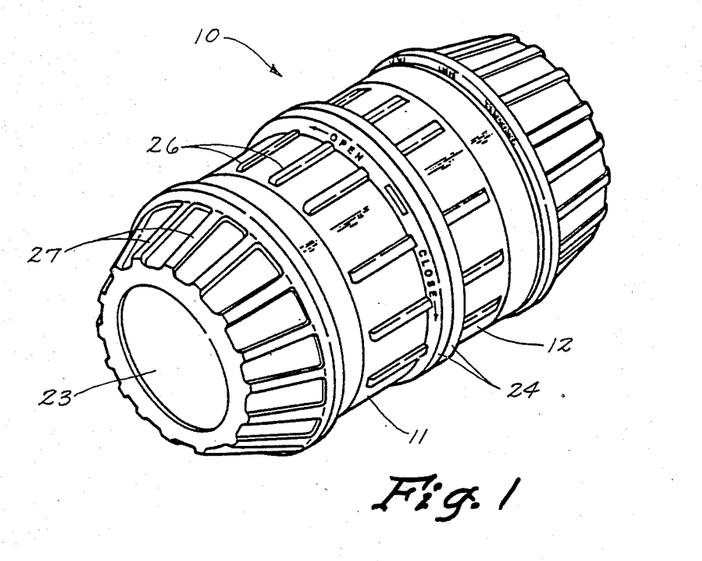
FIG. 1 comprises a perspective view of the first and second container units as attached to one another.

Referring to FIG. 2, the connecting unit (13) includes a plurality of tabs (28) disposed along the rim (24) provided therefore on the base unit (22) of the first container unit (11). Similarly, the second container unit (12) has a plurality of notches (29) formed in the rim (24) provided therefore on the second container unit (12). The tabs (28) of the first container unit (11) can be disposed within the notches (29) of the second container unit (12). The first and second container units (11 and 12) can then be rotated with respect to one another to cause the tabs (28) to become locked within the notches (29). When so joined, the first and second container units (11 and 12) appear as shown in FIG. 1.

Conversely, the first and second container units (11 and 12) can be rotated in the opposite direction with respect to one another so that the tabs (28) can be removed from the interaction with the notches (29). In this position, the first and second container units (11 and 12) can be separated from one another as shown in FIG. 2.

Figure 3:
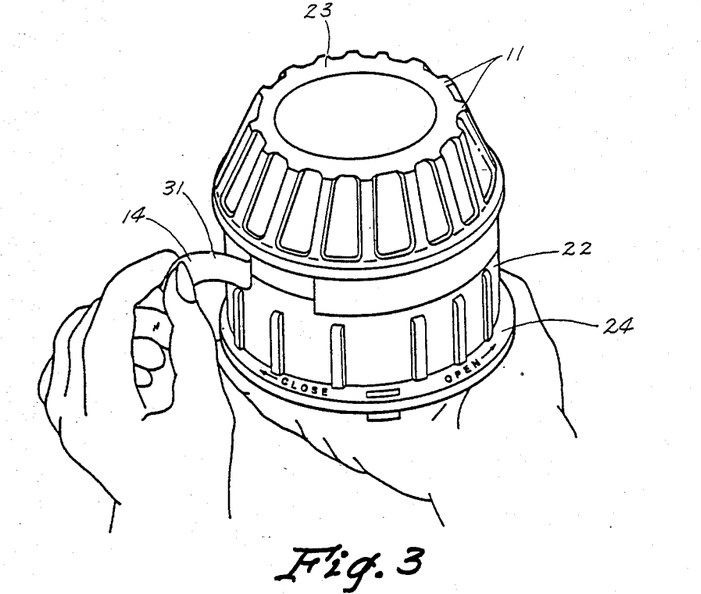
FIG. 3 comprises a perspective view of one of the container units having a sealing tape removed therefrom.

Referring to FIG. 3, each container unit (11) includes an opening unit (14). In this embodiment, the opening unit (14) comprises a strip of adhesive tape (31) that completely surrounds the periphery of the container unit (11). This tape (31) serves to connect the cap unit (23) with the base unit (22).

Figure 4:
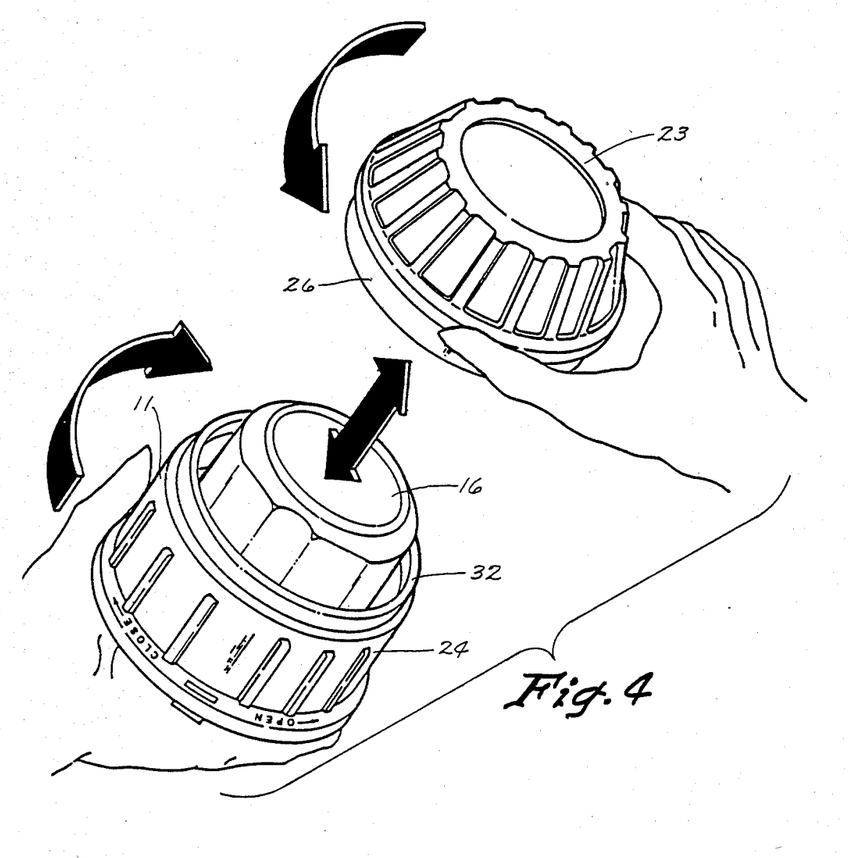
FIG. 4 comprises a perspective of one of the container units being opened.

Referring to FIG. 4, with the tape (31) removed, the cap unit (23) can be removed from the base unit (24) as indicated. The base unit (24) includes a male joinder unit (32) and the cap unit (23) includes a female joinder member (26). So configured, the cap unit (23) can be joined to the base unit (24) by snugly disposing the cap unit (23) over the male joinder member (32) of the base unit (24).

Figure 5:
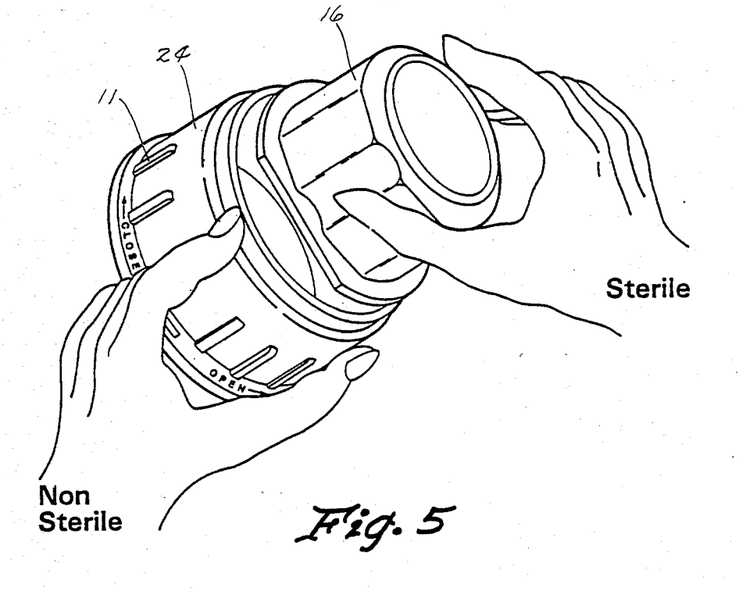
FIG. 5 comprises a perspective view of a secondary container unit being removed from a container unit.
Figure 6:
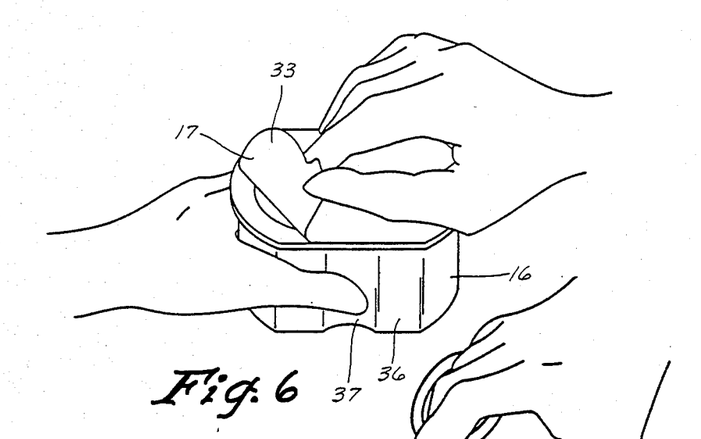
FIG. 6 comprises a perspective view of a secondary container unit being opened.

With the cap unit (23) removed from the base unit (22), it can be seen that the container unit (11) has a secondary container unit (16) contained therein. As shown in FIG. 5, the secondary container unit (16) can be removed from the base unit (24). Referring to FIG. 6, the secondary container unit (16) can then be opened by removing the adhesively attached flexible cover (33) that comprises the secondary container opening unit (17).

Figure 7:
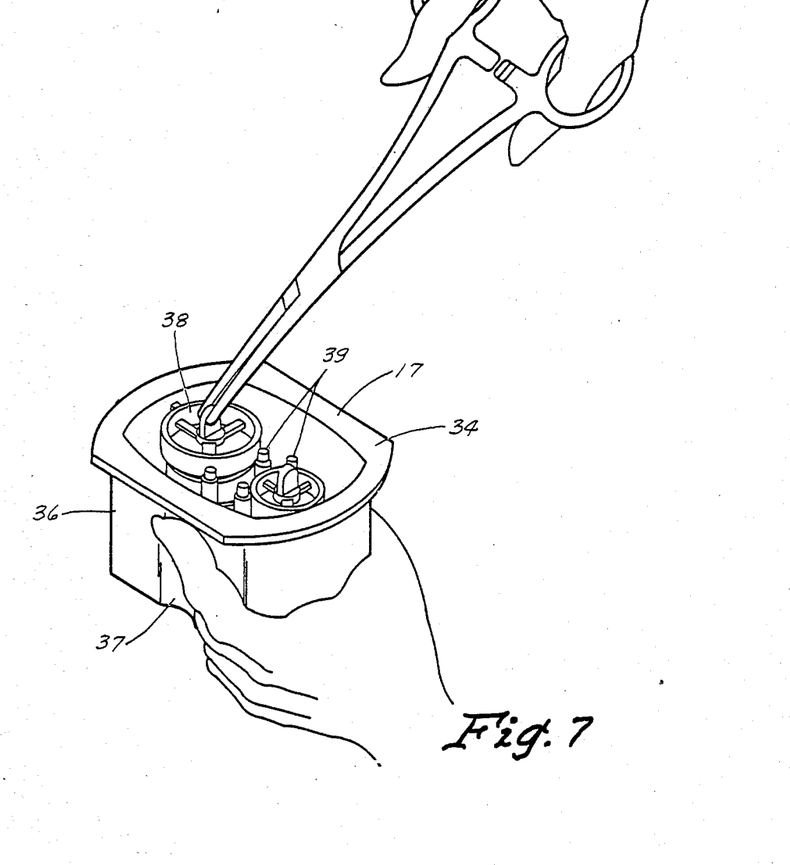
FIG. 7 provides a perspective view of a gauge being removed from a secondary unit.

Referring to FIG. 7, each secondary container unit (17) comprises a container that may be made of plastic or any other suitable material. The upper rim has a flange (34) formed about the periphery thereof to provide adequate surface area for affixment of the adhesively attached flexible cover (33).

With continued reference to FIG. 7, one secondary container unit (17) can be utilized to store a gauge set (38). One or more posts (39) can be attached to the bottom wall of the secondary container unit (17) to assist in maintaining the heart valve orifice measuring gauge (38) in an orderly manner.

Figure 8:
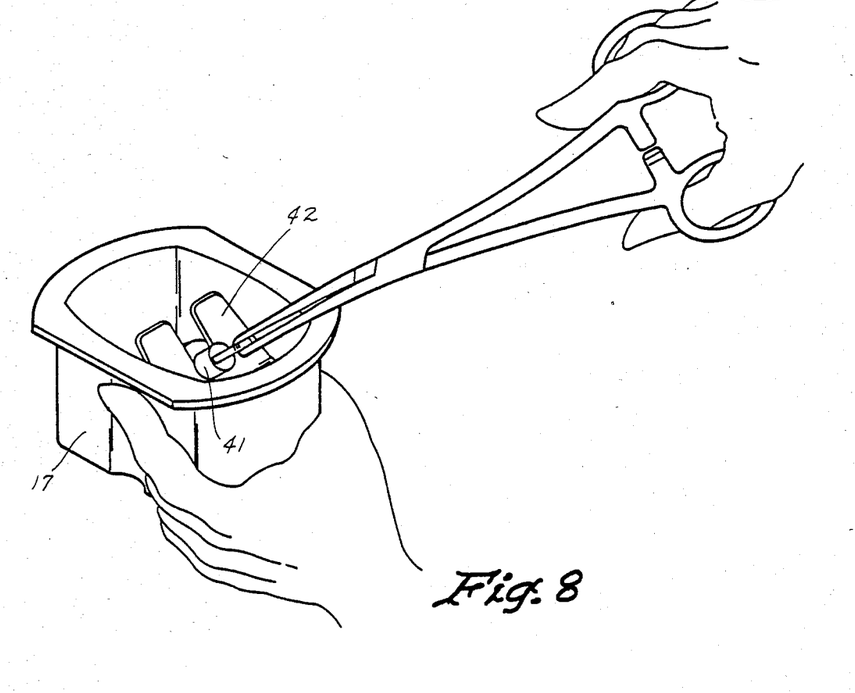
FIG. 8 comprises a perspective view of a prosthetic heart valve being removed from a secondary container unit.

Referring to FIG. 8, the remaining secondary container unit (17) contains a prosthetic heart valve, inclusive of protective packaging for the prosthetic heart valve (41) itself.

Figure 10:
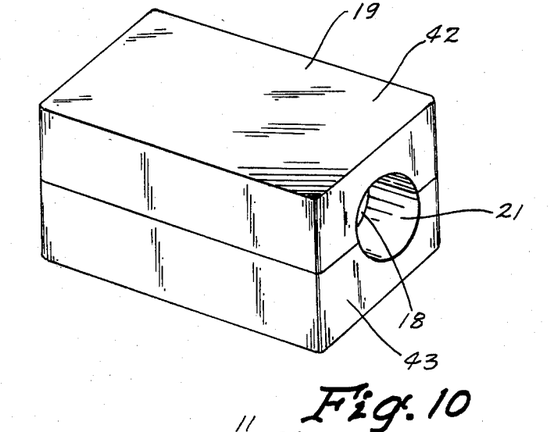
FIG. 10 comprises a perspective view of the package unit.
Figure 11:
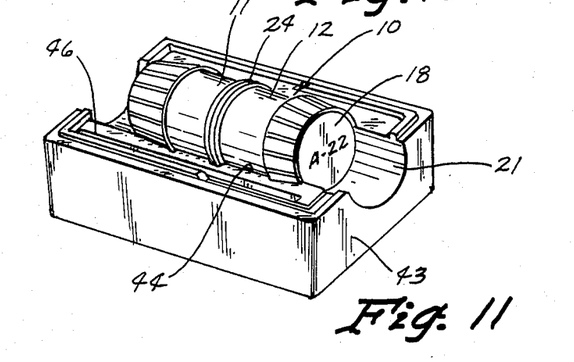
FIG. 11 comprises a perspective view of the first and second container units as disposed within the package unit.

Referring now to FIGS. 10 and 11, the package unit (19) includes a substantially opaque styrofoam shell that may be comprised of a top half (42) and a bottom half (43). As shown in FIG. 11, each half (42 and 43) may have a cavity (44) formed therein to receive the first and second container units (11 and 12).

The package unit (19) includes a window unit (21) that may be comprised of a hole disposed through the styrofoam shell. In the embodiment depicted, both the top and bottom halves of the shell (42 and 43) have holes disposed therethrough such that when the shells are placed together, as shown in FIG. 10, a single hole (21) results. Any number of window units (21) can be provided as desired. At least one such window unit (21) must be provided, however, to allow the object indicia (18) disposed on at least one of the container units (11 and 12) to be visible through the window unit (21).

With reference to FIG. 9, a sleeve unit (22) comprising a four-sided cardboard sleeve may be disposed about the styrofoam shell in order to aid in holding the two halves (42 and 43) together. This sleeve unit (22) can be easily removed or replaced as desired.

Use of the apparatus (10) will now be described.

The storage unit (10) may be retained in inventory with a plurality of other like storage units (10) such that the object indicia (18) can be easily viewed. At the outset of heart valve implantation surgery, a storage unit may be removed from inventory and taking to the operating room.

There, the sleeve unit (22) may be easily withdrawn from the styrofoam shell. Just as easily, the top half (42) of the styrofoam shell may be removed from association with the bottom half (43), thereby exposing the first and second container units (11 and 12).

The first and second container units (11 and 12) may be removed from the bottom half (43) of the styrofoam shell and rotated with respect to one another. The first and second container units (11 and 12) may then be separated from one another as shown in FIG. 2.

The opening unit (14) for the container unit that contains the heart valve orifice measurement gauges set (38) can then be manipulated to allow the cap unit (23) to be removed from the base unit (24). (As shown in FIGS. 3 and 4). The secondary container unit (16) contained within that container unit can then be easily removed as shown in FIG. 5, and the secondary container opening unit (17) removed to allow access to the sterilized gauges (38) container therein as shown in FIG. 7. These gauges can be removed and manipulated through use of a surgical instrument such as a hemostat or clamp.

The heart valve orifice measurement gauges (38) can then be appropriately manipulated to determine the size of the natural heart valve orifice. If the heart valve orifice matches the size of the heart valve contained in the remaining container unit, then this container unit can be opened in the manner described to gain access to the prosthetic heart valve contained therein.

If, however, the prosthetic heart valve contained in the remaining container unit does not match the required size, then a storage unit (10) containing the properly sized prosthetic heart valve (41) can be obtained and removed from inventory.

The container unit containing the correct sized prosthetic heart valve can be removed from the gauges set (38) associated therewith so that the prosthetic heart valve (41) can be obtained in the manner described above. The container unit that contains the first chosen prosthetic heart valve can then be attched to the container unit containing the gauges set (38) that had been previously connected to the second chosen prosthetic heart valve. The recombined container units (11 and 12) can then be returned to the styrofoam shell, reinserted into the sleeve unit (22) and returned to inventory.

As may be desired, instruction material and other written material as may be required by various regulatory agencies can be included within the apparatus (10), by providing a slot (46) in both the top and bottom half (42 and 43) of the styrofoam shell. When so provided, the instruction material will be disposed in both halves when the halves are abutted, hence providing additional structural stability thereto.

Through use of this apparatus, it will be appreciated that each prosthetic heart valve can be supplied to a hospital in conjunction with a sterilized set of disposable heart valve orifice measurement gauges. As properly used, there will always be on hand a set of gauges for use with each prosthetic heart valve.

Obviously, numerous modifications and variations of the present invention are possible in light of the above teachings. It is therefore to be understood that within the scope of the appended claims, the invention may be practiced otherwise than as specifically described therein.

I claim:

1. A storage unit for use in storing a prosthetic heart valve and a plurality of heart valve opening measurement gauges prior to use thereof, comprising:
    (a) first and second container units:
    (b) connecting means for selectively connecting and disconnecting said first and second container units to and from one another;
    (c) first opening means for selectively gaining access to said first container unit but not to said second container unit;
    (d) second opening means for selectively gaining access to said second container unit but not to said first container unit; and
    (e) object indicia visibly disposed on either of said first and second container units to identify the size and type of said prosthetic heart valve stored within said storage unit.

2. The storage unit of claim 1 wherein:
    (a) said first container unit has a first secondary container unit disposed therein; and
    (b) said second container unit has a second secondary container unit disposed therein.

3. The storage unit of claim 2 wherein:
    (a) said first secondary container unit contains said prosthetic heart valve; and
    (b) said second secondary container unit contains said plurality of heart valve opening measurement gauges.

4. The storage unit of claim 3 wherein said first and second container units and said first and second secondary container units are each individually hermetically sealed.

5. The storage unit of claim 1 wherein said connecting means includes:
    (a) a plurality of locking tabs disposed on said first container unit; and
    (b) a plurality of tab receiving notches formed within said second container unit; such that at least some of said tabs may be placed within at least some of said notches, said first and second container units being selectively rotatable with respect to one another to cause said tabs to become selectively locked and unlocked with respect to each other.

6. The storage unit of claim 5 wherein said first and second container units have a substantially similar configuration with respect to one another.

7. The storage unit of claim 1 and further including:
    (a) a substantially opaque package means for substantially surrounding said first and second container units; and
    (b) window means for rendering said object indicia viewable from outside said package means at all times when said first and second container units are disposed within said package means.

8. The storage unit of claim 7 wherein said substantially opaque package means includes two substantially equal halves that may be selectively abutted against one another.

9. The storage unit of claim 8 wherein said window means includes;

(a) a first cavity formed in one said half of said opaque package means; and
(b) a second cavity formed in said remaining one half of said opaque means; such that when said two substantially equal halves are placed in abuttment, said first and second cavities combine to produce a single window.

10. The storage unit of claim 7 and further including sleeve means for at least partially enveloping said package means, without occluding said window means.

* * * * *